(12) United States Patent
Hechler et al.

(10) Patent No.: US 7,772,410 B2
(45) Date of Patent: Aug. 10, 2010

(54) METHOD FOR PRODUCING PHTHALIC ANHYDRIDE

(75) Inventors: Claus Hechler, Ludwigshafen (DE); Gerhard Olbert, Dossenheim (DE)

(73) Assignee: BASF SE, Ludwigshafen (DE)

( * ) Notice: Subject to any disclaimer, the term of this patent is extended or adjusted under 35 U.S.C. 154(b) by 639 days.

(21) Appl. No.: 11/722,449

(22) PCT Filed: Dec. 21, 2005

(86) PCT No.: PCT/EP2005/013774

§ 371 (c)(1),
(2), (4) Date: Jun. 21, 2007

(87) PCT Pub. No.: WO2006/069694

PCT Pub. Date: Jul. 6, 2006

(65) Prior Publication Data

US 2010/0022785 A1     Jan. 28, 2010

(30) Foreign Application Priority Data

Dec. 22, 2004    (DE) ........................ 10 2004 061 770

(51) Int. Cl.
*C07D 307/89*     (2006.01)
(52) U.S. Cl. ..................................... 549/248
(58) Field of Classification Search .................. 549/248
See application file for complete search history.

(56) References Cited

U.S. PATENT DOCUMENTS 5,225,574 A     7/1993    Aichinger et al.

FOREIGN PATENT DOCUMENTS

| DE | 1274569 A1 | 8/1968 |
| DE | 4013051 A1 | 11/1991 |
| DE | 10144857 A1 | 3/2003 |
| EP | 0 453 951 | 10/1991 |

*Primary Examiner*—Bernard Dentz
(74) *Attorney, Agent, or Firm*—Connolly Bove Lodge & Hutz LLP

(57) ABSTRACT

Processes comprising: (a) providing a reactant comprising a component selected from the group consisting of o-xylene, naphthalene and mixtures thereof, and a gas comprising oxygen; (b) reacting the reactant and the gas in a reaction system, in the presence of a catalyst, to form phthalic anhydride; wherein the reaction system comprises: (i) at least two reaction zones, each reaction zone cooled with a coolant; and (ii) an intermediate cooling zone disposed between a first of the at least two reaction zones and a second of the at least two reaction zones; and wherein the coolant entering the first of the at least two reaction zones has a temperature which is more than 20° C. higher than a temperature of the coolant entering the second of the at leas two reaction zones.

15 Claims, 14 Drawing Sheets

METHOD FOR PRODUCING PHTHALIC ANHYDRIDE

CROSS-REFERENCE TO RELATED APPLICATIONS

This application is a national stage application, under 35 U.S.C. §371, of PCT/EP2005/013774, filed Dec. 12, 2005, which claims priority of German Application No. 10 2004 061 770.8, filed Dec. 22, 2004.

BACKGROUND OF THE INVENTION

The invention relates to a process for preparing phthalic anhydride by catalytic partial oxidation of o-xylene and/or naphthalene with a gas comprising oxygen in a plant comprising two or more cooled reaction zones.

In chemical process technology, a multitude of partial oxidation reactions of fluid, i.e. gaseous, liquid or gaseous/liquid, reaction mixtures are known, which are carried out in the presence of heterogeneous particulate catalysts. Such reactions are generally exothermic, frequently strongly exothermic.

Phthalic anhydride is prepared on the industrial scale by partial oxidation of o-xylene and/or naphthalene with a gas comprising oxygen, frequently air, over heterogeneous, especially supported, catalysts. The reaction enthalpy for the oxidation of o-xylene is 1110 kJ/mol and, for naphthalene, 1792 kg/mol of phthalic anhydride formed, i.e. the reaction is strongly exothermic. For inexpensive production with high reactor throughputs, a high loading of the air with reactant is required; these gas mixtures are frequently then ignitable.

To reduce the proportions of undesired intermediates, byproducts and also of reactant in the process gas, which present problems in the product removal from the gas stream and the further workup, it is usually necessary to attain reactant conversions close to 100 mol %.

As in the case of other partial oxidations too, it is typical that, in the preparation of phthalic anhydride, the approach of the reactant conversion to 100% is associated with an increasing proportional rate of total oxidation to carbon monoxide and carbon dioxide. It is also possible at too low a reaction rate for by-products to form, especially phthalide in the case of the synthesis of phthalic anhydride, by which the product quality is impaired. For the reasons mentioned, a high conversion and thus a perceptible yield loss have to be accepted according to the prior art to obtain on-spec product.

Owing to the aging of the catalyst with increasing operating time, it is necessary for a uniform conversion to raise the temperature in the reactor, as a result of which even higher yield losses have to be accepted according to the prior art.

To a certain degree, the yield can be improved by the utilization of an uncooled postreactor in which a limited residual conversion takes place at reduced temperature, as a result of which especially compliance with the product specification is enabled. At the inlet and outlet of the postreactor, the process gas mixture still comprises a very large amount of organic substance and also free oxygen and is generally ignitable. To limit the temperature rise, the conversion of the postreaction has to be strictly limited to avoid runaway of the reaction.

DE-A 101 44 857 discloses a reactor arrangement in which a main reactor designed as a tube bundle reactor, a cooling stage and also a postreactor are arranged in a single casing, the postreactor being an uncooled shaft reactor. This arrangement in one casing keeps the gas volume between main reaction zone and postreaction zone small, with the advantage that the risk of ignition is greatly reduced there. In this way, it is intended that an advantageous yield should be realizable even at loadings of over 100 g of o-xylene per $m^3$ (STP) in the reactant mixture. With the proposed operating mode, an adiabatic reaction in the postreactor, the possible conversion there is, however, greatly restricted for the reasons already mentioned above, so that neither a significant yield improvement nor in particular any prolonging of the catalyst lifetime is possible in this way.

DE-A 40 13 051 discloses a process for preparing phthalic anhydride using a tube bundle reactor comprising at least two successive reaction zones in flow direction with separate salt bath cooling, the salt bath temperature in the first reaction zone being kept from 2 to 20° higher than the salt bath temperature in the remaining reaction zones. This process achieves an improved yield of phthalic anhydride, since the temperature is adjusted better to the reaction kinetics. In spite of this, high yield losses remain owing to the high temperature level in both cooling zones, at which the required high conversion of approx. 99% mol % can be achieved.

BRIEF SUMMARY OF THE INVENTION

It was accordingly an object of the invention to provide an improved process for preparing phthalic anhydride, by which a higher proportion of the residual conversion can be realized in process stages which are attached downstream of the synthesis in the main reactor. The process should in particular also be adaptable flexibly to different load ranges without yield losses.

The solution consists in a process for preparing phthalic anhydride by catalytic partial oxidation of o-xylene and/or naphthalene with a gas comprising oxygen in a plant comprising two or more reaction zones cooled with a coolant,
one or more devices arranged between the reaction zones for intermediate cooling of the reaction mixture between the reaction zones, the temperature of the coolant on entry into the second or into the further reaction zones decreasing compared to the temperature of the coolant on entry into the first reaction zone, wherein the temperature of the coolant on entry into the first reaction zone is more than 20° higher than the temperature of the coolant on entry into the second or into the further reaction zones.

It is known that the conversion rate in postreactors for preparing phthalic anhydride is greatly limited, since the postreaction introduces heat into the reaction gas stream and heats it, and then the further reaction of already formed product of value to the products of total oxidation, carbon monoxide and carbon dioxide, subsequently sets in progressively, with the consequence of a reduced yield and also the risk that the postreactor runs away.

It has been found that, surprisingly, contrary to previous assumptions, it is possible to achieve virtually full conversion of o-xylene and also of the phthalide by-product to the phthalic anhydride product of value without noticeable additional yield losses provided that suitable heat removal in the postreactor prevents too high a temperature rise even when residual conversions in the range from 5 to 10%, but also up to 15% or even up to 20%, of the molar overall conversion are shifted into the postreactor, even though this postreaction is at a temperature level distinctly below the temperature level known to be necessary for the reaction of o-xylene to phthalic anhydride at high conversion rates (>70%).

DETAILED DESCRIPTION OF THE INVENTION

The invention is not restricted with regard to the specific catalysts used: it is possible to use all known catalysts for preparing phthalic anhydride, especially supported catalysts with an active composition comprising one or more of the elements vanadium, titanium or phosphorus, for example in the form of their oxides. Suitable catalysts are disclosed, for example, in the thesis "In situ Charakterisierung von Vanadiumoxid/Titanoxid-Katalysatoren bei der partiellen Oxidation von o-Xylol zu Phthalsäureanhydrid" [In-situ characterization of vanadium oxide/titanium oxide catalysts in the partial oxidation of o-xylene to phthalic anhydride] by Dipl.-Ing. M. Brust, Faculty of Chemical Engineering of the University of Karlsruhe, date of colloquium: Dec. 20, 1999, and the literature referenced there. It is also possible to use catalysts with structured activity, i.e. with different activity in individual reaction zones or regions thereof. It is possible in principle to use unsupported catalysts consisting entirely of active composition, for example in sphere, cylinder, extrudate or ring form, but also moldings coated with active composition, for example spheres or rings. The typical longitudinal dimensions or diameters of these moldings are in the range from 1 mm to 10 mm, although frequently from 3 mm to 8 mm and often from 5 mm to 7 mm are encountered.

Particularly advantageously, the catalyst can be optimized for yield in the first reaction zone or the main reactor, since significant proportions of the residual conversion can be achieved in downstream reaction zones or in the postreactor.

The reactant used may be o-xylene, naphthalene or a mixture of o-xylene and naphthalene.

The gas which comprises oxygen and is required for the partial oxidation is preferably air.

The two or more cooled reaction zones may be accommodated in a single apparatus or else in two or more separate apparatuses. Particular preference is given to an embodiment with two reaction zones, a first reaction zone in a main reactor and a second reaction zone in a postreactor.

The reactors may be cylindrical, but also have other geometries, for example parallelepipedic, in particular cuboidal.

The reaction zones can be cooled with all customary heat carriers. Particularly advantageously, the devices for accommodating the heat carriers may be designed as thermoplates, through which a coolant flows, preferably water, which evaporates at the same time (so-called evaporative cooling).

Intermediate coolers for the reaction mixture are arranged between the reaction zones.

The process may be carried out particularly advantageously in an apparatus with thermoplates, in which case main reactor, intermediate cooler and postreactor are arranged in the same apparatus. In this case, in the main reactor and also in the postreactor, beds of the solid-state catalyst are provided in the main reactor in the interstices between the thermoplates, through which the reaction gas mixture is passed.

An inert bed may preferably be provided in the intermediate cooler. It is also possible to differentiate the intermediate cooler and the postreactor only in that the region which functions as the intermediate cooler is left empty or in that an inert bed is provided therein and in that, in the region which functions as the postreactor, a bed is provided as a solid-state catalyst. The intermediate cooler and the postreactor are preferably attached to a single cooling circuit which is separated from the cooling circuit for the main reactor.

The terms heat exchanger plates, heat transferrer plates or thermoplates are used substantially synonymously.

Heat transferrer plates are defined predominantly as sheetlike structures which have an interior provided with inlet and outlet lines and having a low thickness in comparison to the surface area. They are generally produced from metal sheets, frequently from steel sheets. However, depending on the application case, in particular the properties of the reaction medium and of the heat carrier, special, in particular corrosion-resistant, or else coated materials may be used. The inlet and outlet devices for the heat carriers are generally arranged at opposite ends of the heat exchange plates. The heat carriers used are frequently water, or else Diphyl® (mixture of from 70 to 75% by weight of diphenyl ether and from 25 to 30% by weight of diphenyl), which sometimes also evaporate in a boiling operation; it is also possible to use other organic heat carriers having a low vapor pressure and also ionic liquids.

The use of ionic liquids as heat carriers is described in DE-A 103 16 418. Preference is given to ionic liquids which contain a sulfate, phosphate, borate or silicate anion. Also particularly suitable are ionic liquids which contain a monovalent metal cation, in particular an alkali metal cation, and also a further cation, in particular an imidazolium cation. Also advantageous are ionic liquids which contain an imidazolium, pyridinium or phosphonium cation as the cation.

The term thermoplates is used in particular for heat transferrer plates whose single, usually two, metal plates are joined together by point and/or roll welds and are frequently shaped using hydraulic pressure plastically to form pockets.

The process according to the invention can preferably be carried out by using a reactor as described in DE 103 33 866, whose disclosure content is hereby incorporated fully into the present patent application, i.e. a reactor comprising
  one or more cuboidal thermoplate modules which are each formed from two or more rectangular thermoplates arranged parallel to each other while in each case leaving a gap which can be filled with the heterogeneous particulate catalyst and is flowed through by the fluid reaction mixture, the heat of reaction being absorbed by a heat carrier which flows through the thermoplates and in doing so at least partly evaporates, and also comprising
  a predominantly cylindrical shell which releases the pressure at the thermoplate modules, completely surrounds them and comprises a cylinder jacket and hoods which conclude it at both ends and whose longitudinal axis is aligned parallel to the plane of the thermoplates, and also comprising
  one or more sealing elements which are arranged in such a way that the fluid reaction mixture, apart from flowing through the reactor interior spaces bounded by the hoods, only flows through the gap.

They are thus thermoplate modules which comprise thermoplates, through which a heat carrier flows, absorbs the heat of reaction and at the same time at least partly evaporates, and are configured with a cuboidal shape and are installed with pressure release in a predominantly cylindrical shell which completely surrounds them.

The plate modules are formed from in each case two or more rectangular thermoplates which are arranged parallel to each other while in each case leaving a gap.

The thermoplates are manufactured from corrosion-resistant materials, preferably from stainless steel, for example having the materials number 1.4541 or 1.4404, 1.4571 or 1.4406, 1.4539 or else 1.4547, or from other alloyed steels.

The material thickness of the metal sheets used for this purpose may be selected between 1 and 4 mm, 1.5 and 3 mm, or else between 2 and 2.5 mm, or to be 2.5 mm or to be 3 mm.

In general, two rectangular metal sheets may be joined at the longitudinal and end sides to give a thermoplate, in which case a roll seam or lateral weld joint or a combination of both is possible so that the space in which the heat carrier is later disposed is sealed on all sides. The edge of the thermoplates is advantageously removed at or even in the lateral roll seam of the longitudinal edge so that the edge region, which is poorly cooled if at all, and in which catalyst is usually also installed, has a very low geometric expansion.

The metal sheets are joined together by point welding distributed over the rectangular surface. An at least partial connection by straight or else curved and also circular roll seams is also possible. It is also possible for the volume flowed through by the heat carrier to be divided by additional roll seams into a plurality of separate regions.

One possibility of arranging the weld points on the thermoplates is in rows with equidistant point separations of from 30 to 80 mm or else from 35 to 70 mm although separations of 40 to 60 mm are also possible, a further embodiment being separations of from 45 to 50 mm and also from 46 to 48 mm. Typically, as a result of the manufacture, the point separations vary by up to ±1 mm and the weld points of immediately adjacent rows, viewed in the longitudinal direction of the plates, are each arranged offset by half a weld point separation. The rows of the point welds in the longitudinal direction of the plates may equidistant with separations of from 5 to 50 mm, or else from 8 to 25 mm, although separations of from 10 to 20 mm and also from 12 to 14 mm, may also be used. Moreover, pairings of the weld point separations and row separations mentioned which are adapted to the application case are also possible. The row separations may be in a defined geometric relationship to the point separation, typically ¼ of the point separations or somewhat lower, so that there is a defined uniform expansion of the thermoplates in the course of the production. For predefined weld point and row separations, a corresponding number of weld points per $m^2$ of plate surface area is designated.

The width of the thermoplates is limited substantially by manufacturing technology considerations and may be between 100 and 2500 mm, or else between 500 and 1500 mm. The length of the thermoplates is dependent upon the reaction, in particular upon the temperature profile of the reaction, and may be between 500 and 7000 mm, or else between 3000 and 4000 mm.

In each case two or more thermoplates are arranged parallel and separated from one another to form a thermoplate module. This results in shaftlike gaps forming between immediately adjacent plates which, at the narrowest points of the plate separation, for example, have a width of between 8 and 150 mm, or else from 10 to 100 mm. One possible embodiment is also widths of from 12 to 50 mm or else from 14 to 25 mm, although from 16 to 20 mm may also be selected. A gap separation of 17 mm has also been tested.

Between the individual thermoplates of a thermoplate module, for example in the case of large-surface area plates, spacers can additionally be installed in order to prevent deformations which can change plate separation or position. To install these spacers, sections of the metal plates can be removed from the flow region of the heat carrier, for example by circular roll seams, in order, for example, to be able to introduce holes into the plates for securing screws of the spacers.

The gaps may have the same separation, but, if required, the gaps may also be of different width when the reaction permits it or the desired reaction requires it, or apparatus or cooling technology advantages can be achieved.

The gaps of a thermoplate module filled with catalyst particles may be sealed with respect to each other, for example sealed by welding, or else be joined together on the process side, so that pressure equalization can take place between the gaps flowed through with process gas.

To adjust the desired gap separation when joining the individual thermoplates together to form a module, the plates are secured in their position and with separation. One possibility is the use of two lateral boundary plates for each module, at or into which the individual thermoplates are effected by mechanical securing, for example by introducing the lateral plate edges into grooves or slots which have been introduced beforehand, or else by cohesive securing such as welding to a flat plate, in which case the plate can be sealed by welding over the entire length or else at least partially only tacked, in order to enable pressure equalization of the gaps. An alternative embodiment is the use of tubular, angled or curved plate parts which are each tacked between two plates and sealed from the outside by welding.

The weld points of immediately adjacent thermoplates may be opposite each other or offset from one other.

In general, preference is given for manufacturing reasons to configuring the arrangement with two or more cuboidal thermoplate modules with in each case identical dimensions. In the case of arrangements of 10 or 14 thermoplate modules, it may be advantageous for the compactness of the overall apparatus to select two module types having different edge lengths or different edge length ratios.

Preference is given to arrangements of 4, 7, 10 or 14 thermoplate modules having in each case identical dimensions. The projection surface, visible in the flow direction, of a module may be square, or else rectangular is a side ratio of 1.1 or else 1.2. Combinations of 7, 10 or 14 modules having rectangular module projections are advantageous, so that the diameter of the external cylindrical shell is minimized. Particularly advantageous geometric arrangements can be achieved when, as detailed above, a number of 4, 7 or 14 thermoplate modules is selected.

It should advantageously be possible in this context to exchange the thermoplate modules individually, for example in the case of leaks, deformations of the thermoplates or in the case of problems which affect the catalyst.

Advantageously, the thermoplate modules are each arranged in a pressure-stable, rectangular stabilization frame.

Each thermoplate module is advantageously kept in position by a suitable guide, for example by the rectangular stabilization frames, with a laterally penetrating wall, or, for example, by an angle construction.

In one embodiment, the rectangular stabilization frames of adjacent thermoplate modules are sealed with respect to each other. This prevents bypass flow of the reaction mixture between the individual thermoplate modules.

The installation of cuboidal thermoplate modules into a predominantly cylindrical pressure-rated shell results in relatively large free intermediate spaces remaining at the edge toward the cylindrical jacket wall of the shell, in which accumulation, side reactions or decomposition of the material product can take place. Cleaning or decontamination of product, for example in the event of the necessity of assembly operations, is only possible there with great difficulty. It is therefore advantageous to separate this intermediate space from the reaction chamber, i.e. from the gaps between in each case immediately adjacent thermoplates.

To this end, the intermediate space between the thermoplate modules and the predominantly cylindrical shell is sealed at the lower end of the thermoplate module with a holding base. In order to prevent bypass flow of the reaction mixture, the bearing or holding base should seal the intermediate space in a gas-tight manner.

Advantageously, the intermediate space between the thermoplate modules and the predominantly cylindrical shell may also be sealed at the upper end of the thermoplate module by a metal sheet cover. However, a gas-tight seal is not necessary for this purpose; it is possible in one embodiment to configure the metal sheet cover with orifices.

The metal sheet cover at the upper end of the intermediate space between the thermoplate modules and the predominantly cylindrical shell may advantageously also be configured similarly to a valve tray.

The venting of the gas used to apply pressure may also be performed by means of an overflow unit, configured as a perforated plate, valve or force-loaded (for example with a spring or gas pressure), self-regulating unit, also in combination with a blowback safeguard. These overflow units may also be disposed outside the cylindrical external shell.

The upper metal sheet cover may rest on struts which additionally stabilize the rectangular stabilization frames in which the thermoplate modules are installed.

The intermediate space between the thermoplate modules and the predominantly cylindrical shell may advantageously be filled with inert materials, in order to reduce the free gas volume there and in order to prevent gas convection which may lead, for example, to uncontrolled heat release.

In the cylindrical shell, it is advantageous to provide nozzles for the inlet and outlet of the inert bed material which are configured in suitable size and mounted at a suitable angle in such a way that blockage-free filling and emptying is possible under the force of gravity. Possible embodiments of the nozzles are nominal widths of 80, 100, 150 or 200 mm.

The inert material bed used may in principle be any chemically inert and sufficiently mechanically and thermally stable material, for example expanded perlite and/or expanded vermiculite.

It is possible to charge the intermediate space between the thermoplate modules and the predominantly cylindrical shell, which may be filled with inert material, with a gas pressure.

The application of pressure may be substantially constant and advantageously brought about by the pressure-regulated input and output of nitrogen. The regulation signal selected may be, for example, the pressure differential between the pressure in the intermediate space between the thermoplate modules and the predominantly cylindrical shell and the pressure at the lower end of the catalyst bed in the gaps of the thermoplate modules or at the upper end thereof. Advantageously, the differential pressure signal may be corrected by an offset value; a mean value, in particular the arithmetic mean value, of the pressure over the height of the catalyst bed may preferably be selected as the regulation signal.

To apply pressure, appropriate nozzles and/or an internal ring line having small drillholes, which are preferably directed downward, may be provided in the predominantly cylindrical shell.

Alternatively, it is also possible to bring about the application of pressure with continuous flow through the intermediate space with a gas which is inert or intrinsic to the process, in particular nitrogen or cycle gas.

The gas used to apply pressure is advantageously combined with the fluid reaction mixture at its outlet from the thermoplate modules, generally still within the predominantly cylindrical shell of the reactor. The outlet points of the gas used for pressure charging are advantageously located in flow dead zones of the fluid reaction mixture, in order to purge them.

The volume flow rate of the gas used to apply pressure will generally be significantly less than the volume flow rate of the fluid reaction mixture and is advantageously selected in such a way that it is not harmful to the reaction in process technology terms.

The thermoplate modules should advantageously each be individually exchangeable, in order that, as already outlined above, problems which occur, for example leakages, deformations of the thermoplates or problems with the catalyst, can be remedied in a targeted manner. For this purpose, it is advantageous to configure the thermoplate modules with some play with respect to the wall of the rectangular stabilization frames.

Since the thermoplate modules in this advantageous embodiment thus rest in the rectangular stabilization frames without sealing, bypass flows of the reaction medium may occur. In order to prevent this, the sites between the thermoplate modules and the rectangular stabilization frames where there is no seal are sealed in a suitable manner, for example with metal sheet strips which are mounted on the exterior of the thermoplate modules and press onto the wall of the rectangular stabilization frame when inserted into it. Alternatively, gas-tight metal sheet covers and connections, for example in the form of weld lip seals are possible.

Once the thermoplate modules have been inserted into the rectangular stabilization frames, they can be sealed with respect to the holding base, which seals the intermediate space between the thermoplate modules and the predominantly cylindrical shell at the lower end of the thermoplate modules. It is possible in principle to use any known sealing means for this purpose. These may be, for example, conventional seals which, for example, are additionally screw-secured.

It is also possible to bring about the sealing by weld lips, for example, by a variant in which a weld lip is secured to the holding base and a second weld lip to the outer edge of the thermoplate module or of the rectangular stabilization frame. Both weld lips are configured in such a way that they fit together geometrically and can be welded together. To exchange the thermoplate module, the weld seam is separated and, if required, renewed.

The thermoplate modules can be tensioned from above with the rectangular stabilization frames by a device. Sufficient tensile pressure from above ensures adequate surface pressure on the seal and advantageous securing of the thermoplate modules.

It is not obligatory for the rectangular stabilization frames to be sealed with respect to each other, as long as an impermissible bypass flow past the gaps is prevented. It is also possible to connect the rectangular stabilization frames together with small drillholes, through which the inert gas can flow in from the intermediate space and between thermoplate modules and the predominantly cylindrical shell, which prevents reactions in the space between the thermoplate module and the rectangular stabilization frame.

The thermoplate modules may additionally have guiding and directing elements on the exterior. It is possible, for example, to provide corner brackets of any form on the corners of these elements and conical metal sheet strips on their side. It is also advantageous to mount attachment devices or attachment auxiliaries on the modules, such as eyes, loops or threaded drillholes, in order to enable simple insertion by means of a hoist or, for example, of a crane. To insert the thermoplate modules by crane, they can also be held on tie bars which reach vertically through the initially empty gap down to the lower edge of the plates and are connected there to a transverse support to take up the load.

In a particular embodiment, the outermost thermoplate of a thermoplate module, at the exterior thereof, is formed from a thicker and therefore more stable metal sheet than the other metal sheets used to produce the thermoplates.

To compensate for the thermal expansion, annular compensators in particular are advantageously provided in or on the holding base which seals the intermediate space between the thermoplate modules and the predominantly cylindrical shell at the lower end of the thermoplate modules. Annular compensation with an approximately z-shaped profile viewed in the direction at right angles to the surface of the metal sheet base is particularly suitable. However, other conventional, wave-shaped compensators are equally suitable.

Preference is also given to also providing compensators for the axial and/or radial expansion in or on the metal sheet cover at the upper end of the intermediate space between thermoplate modules and predominantly cylindrical shell.

Each thermoplate module is supplied with the heat carrier by one or more distribution devices. The heat carrier, after flowing through the interior in the individual thermoplates, is removed at the other end of the thermoplate module via one or more collection devices. Since, in accordance with the invention, a heat carrier is used which absorbs the heat of reaction released and in doing so partly evaporates, it is particularly advantageous for the adjustment of the flow rates to provide in each case one distribution device, but two collection devices, per thermoplate module.

The distribution and collection devices are preferably configured in such a way that they each have a compensation for the accommodation of the thermal expansion of the thermoplate modules relative to the surrounding predominantly cylindrical shell. Compensation is possible here, for example, by a curved pipeline design.

To accommodate the thermal expansion of the thermoplate modules relative to the surrounding predominantly cylindrical shell, it is possible to ensure a suitable curved or Z- or omega-shaped geometric configuration of the tubing of the distribution and collection devices for the heat carrier flowing through the thermoplates. In a further embodiment, this compensation may be effected by axial or lateral compensators, in which case any pipe support required may be effected on an internal support structure.

Particular preference is given to configuring the collection tubes in the thermoplates for the feed and distribution, and also collection and removal, of the heat carrier by welding into a slotted tray as follows: the individual thermoplates of a module are initially joined to a channel-shaped metal sheet which is curved toward the interior of the thermoplates and has an approximately semicircular cross section and also orifices or slots for the output of the heat carrier. At this stage of manufacture, it is possible to check that the weldings into the slotted tray are free of manufacturing faults, either in a representative specimen or else in the whole area, for example by X-ray. Subsequently, this first, approximately channel-shaped metal sheet is joined on both longitudinal sides to a second, similarly shaped metal sheet, except having opposite curvature and no orifices or slots, in particular by longitudinal seam welding, to form a tubular component having virtually circular cross section. The two ends of this tubular component are sealed by lids which may optionally be strengthened by an internal tie rod.

In a further embodiment, it is also possible to directly weld tube parts having a relatively small nominal width of, for example, from 4 to 30 mm, onto the thermoplates, frequently onto the metal sheet edges, to feed and remove the heat carrier.

The gaps between the individual thermoplates of each thermoplate module serve to accommodate the heterogeneous particulate catalyst.

In order to rule out flow of the catalyst particles out of the gaps under the influence of gravity, suitable catalyst-retaining grates have to be provided at the lower end thereof. This may be effected, for example, with perforated or mesh plates, and it is particularly advantageous for this purpose to use edge gap sieves, which ensure good retention of the catalyst with simultaneously high dimensional stability and low pressure drop for the reaction medium flowing through.

The catalyst-retaining grates may be installed, for example, in such a way that they can be swiveled.

It is particularly advantageous when the distribution devices for the heat carrier to the thermoplates are installed in such a way that the lateral separations from the distribution devices to the edge of the thermoplate assembly are the same, so that only a single type of catalyst-retaining grate is required. In each case two catalyst-retaining grates are advantageously provided per thermoplate module, i.e. on both sides of the distribution device for the heat carrier.

The catalyst-retaining grates are advantageously dimensioned in such a way that they can be installed and deinstalled via the manholes in the approximately cylindrical shell. The manholes frequently have an internal diameter of 700 mm. Correspondingly, preference is given to an edge length for the catalyst inlay grates of 650 mm.

In a further embodiment, it is possible to further divide these retaining grates into smaller units, but also to seal each gap or each gap half individually, so that it can also be emptied separately.

Alternatively, it is also possible to fill the thermoplate modules with catalyst before they are installed into the reactor, i.e. outside the reactor.

The shell surrounding the thermoplate modules has been described above as predominantly cylindrical. In this context, this means that it has a cylinder jacket with circular cross section which is sealed at both ends in each case by a hood.

The predominantly cylindrical shell is generally installed vertically.

The fluid reaction medium is passed into the reactor interior via one hood, frequently via the lower hood, flows through the gap which is filled with the heterogeneous particulate catalyst and is between the individual thermoplates, and is removed at the other end of the reactor, via the other, frequently the upper, hood.

The hoods are preferably manufactured from stainless steel or are stainless steel-plated.

The hoods may be connected to the cylinder jacket of the shell by secure welding or separably, for example via a flange connection. The flange connection may be configured in such a way that it can be lowered by means of a hydraulic system.

It is advantageously possible to reach the circumference of the hoods on foot via one or more manholes which generally have a diameter of 700 mm. For this purpose, a widened cylindrical section is advantageous, which, like the hood, is, for example, manufactured from stainless steel or is stainless steel-plated.

It is possible via the manholes in the hoods to access the upper side of the modules, so that the catalyst can easily be introduced into the gaps between the thermoplates, and the lower side of the modules, so that the retaining grates can be installed and deinstalled easily.

To deinstall the catalyst, devices may additionally be installed in the lower hood to retain auxiliaries and to collect the catalyst which may have already been installed in the course of operation, and also one or more nozzles to discharge the catalyst.

The material used for the intermediate space between the thermoplate modules and the interior wall of the predominantly cylindrical shell sealing holding base, and for the rectangular stabilization frames for the thermoplate modules too, may be carbon steel. Alternatively, it is possible to use stainless steel for this purpose.

In one or both hoods, it is advantageous to install nozzles, through which multithermoelements can be introduced into the individual thermoplate modules. In addition, nozzles may be mounted there for further field instruments and process analysis devices.

Preference is given to providing, in the cylindrical jacket of the predominantly cylindrical shell, one or more compensators to accommodate preferably the axial thermal expansion.

The heat carrier medium used may be feed water as typically utilized in power stations for steam generation and corresponding to the prior art (Technische Regeln für Dampfkessel [Technical rules for vapor vessels] (TRD 611 of Oct. 15, 1996 in BArbB1. December 1996 p. 84, last altered on Jun. 25, 2001 in BArbB1. August 2001 p. 108). Typical parameters of the feed water may be: conductivity less than 0.4, or less than 0.2, microsiemen/cm, calcium and magnesium hardness less than 0.0005 millimole per liter or below the detection limit, sodium less than 5 micrograms per liter, silicon dioxide less than 20 micrograms per liter, iron less than 50 micrograms per liter and oxygen less than 20 micrograms per liter, and a total content of dissolved carbon of less than 0.2 milligram per liter. In addition, the feed water should be low in or free of halogen, in particular chlorine. It is also possible to condition the feed water in a targeted manner, for example by adding auxiliaries such as hydrazine, ammonia, and in particular to make it alkaline; in addition, corrosion inhibitors can be added to the feed water.

The upper hood, through which the reaction medium leaves the reactor in the above-described preferred process control, may consist of carbon steel.

In order to ensure access to the thermoplate modules for the purpose of repair or exchange, it likewise has to be possible to remove the upper hood. When there is no flange connection, the upper hood can be removed and welded on again after module assembly.

It is possible to integrate the steam removed from the thermoplates into different steam rails.

The reactor may optionally be attached to two steam rails, one of which has a higher pressure and is utilized for the heating of the reactor to operating temperature.

It is advantageous to operate on only one steam rail.

The reactor can preferably be operated with natural circulation of the coolant, water, and a ratio of feed water to steam of generally from 3 to 12, preferably from 5 to 10.

It is also possible to operate with forced circulation, in which case a wider load variation of the cooling is possible. To this end, the feed water is fed at a higher pressure than present in the cooling system, for example by means of a pump.

The feed water circulation rate in the distribution devices may be set between 0.5 and 3.0 m/s, or else from 1.0 to 2.0 m/s, and the water circulation number between 3 and 12. The flow rate of the biphasic flow (steam/water) in the collection devices may be between 0.5 and 15 m/s, or else between 2.0 and 6.0 m/s.

Particular preference is given to carrying out the heating of the thermoplate modules to start up the reactor from the same heat carrier network into which the heat is removed by at least partly evaporated heat carrier medium in the course of reaction operation.

The regulation of the steam pressure in the cooling system makes it possible to precisely adjust the cooling temperature. Experience has shown that the thermoplates can be operated up to a pressure of about 80 bar in the coolant. The reactor according to the invention enables direct steam generation at pressure levels up to 80 bar.

Alternatively to the embodiment with thermoplates, it is, however, also possible to form one, more or all of the cooled reaction zones, especially the main reactor and the postreactor, as individual tube bundle apparatuses or else as individual zones in a single tube bundle apparatus. In particular, the first reaction zone may be designed as a tube bundle apparatus and the second or the further reaction zones as apparatuses with thermoplates.

In the embodiment with main reactor and postreactor as separate tube bundle apparatuses, the postreactor may advantageously be designed with larger tube diameter compared to the main reactor. In all variants with tube bundle apparatuses, the catalyst is generally installed as a bed into the tubes and the heat of reaction is removed via a heat carrier which circulates through the intermediate space around the catalyst tubes.

The first reaction zone or the main reactor is preferably at a temperature of the coolant on entry into the first reaction zone or into the main reactor in the range from 320 to 380° C., and the temperature of the coolant on entry into the second or the further reaction zones or into the postreactor is in the range from 250 to 320° C., preferably in the range from 270 to 300° C., more preferably in the range from 280 to 290° C.

The second or the further reaction zones or the postreactor are operated at from 5 to 10% of the overall conversion in the plant, preferably up to 15%, more preferably up to 20% of the overall conversion in the plant.

In the process according to the invention, it is possible to operate with high loadings of the air with reactants to be oxidized, in particular with loadings of from 30 to 20 g of o-xylene per $m^3$/h of reaction air under standard conditions (0° C. and 1.013 bar absolute), the amounts used typically being from 60 to 110 g and very frequently from 80 to 105 g of o-xylene per $m^3$/h of reaction air under standard conditions.

The process according to the invention enables high flexibility by virtue of the possibility of reacting to different load ranges without yield losses. In particular, it is also possible, for example, to balance age-related performance differences of main reactor catalysts.

Existing plants can be retrofitted in a simple manner to carry out the process according to the invention.

It is possible to use catalysts of simple structure, in particular inexpensive standard catalysts, and it is possible to optimize the catalyst for yield in the main reactor, Overall, improved overall selectivity and yield are achieved compared to known processes.

The invention is illustrated in detail below with reference to a drawing:

Figure 1:
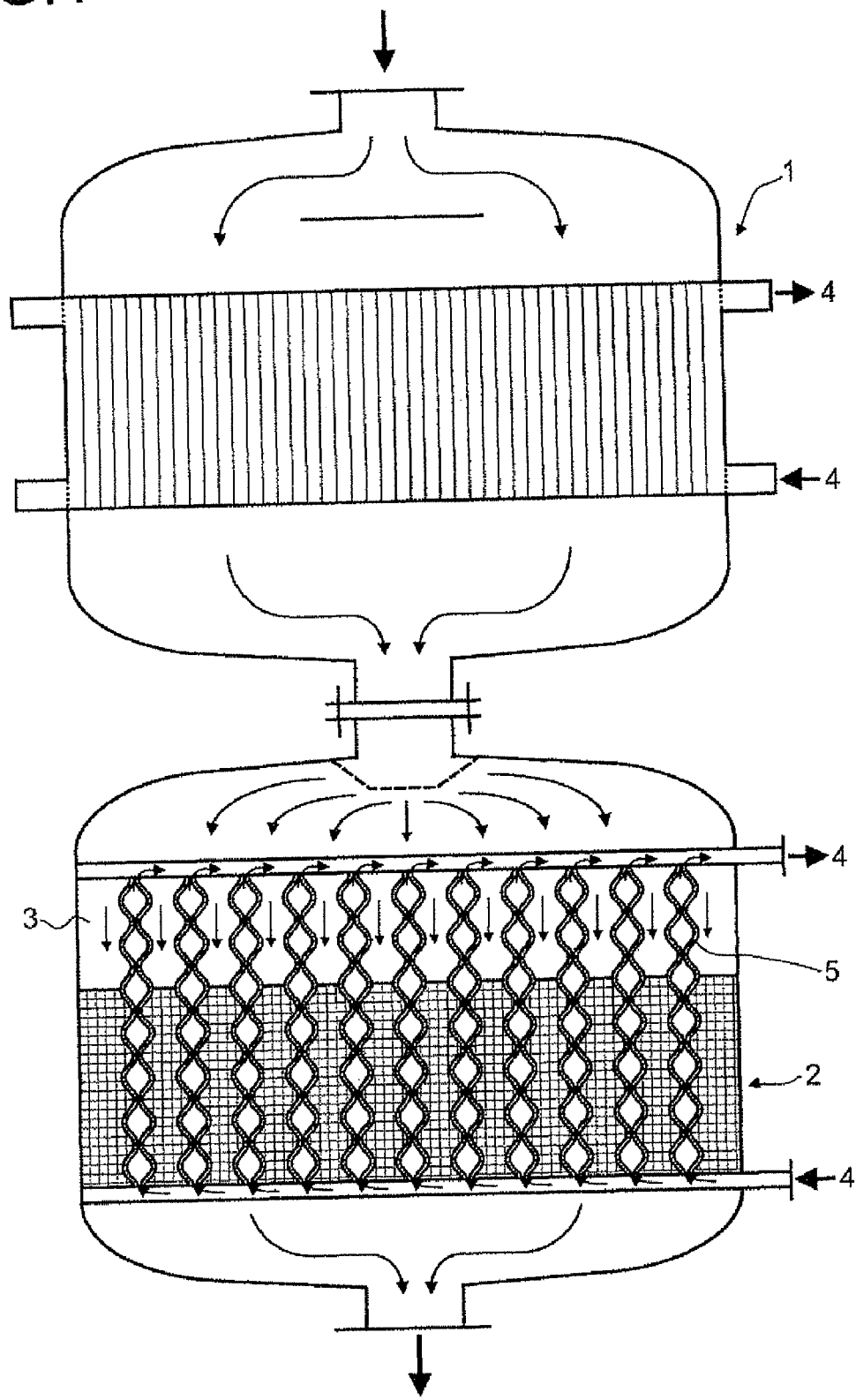
FIG. 1 a schematic illustration of a first embodiment of an inventive plant with main reactor and postreactor, FIG. 2 a variant of the embodiment shown in FIG. 1, FIG. 3 an embodiment with integration of all reaction zones in a single apparatus, FIGS. 4 to 7 further variants of the embodiment shown in FIG. 3, FIG. 8 a further variant of the embodiment shown in FIG. 1, FIGS. 9A and 9B the schematic representation of preferred embodiments with main reactor and postreactor with sectional illustration in FIG. 9C and FIGS. 10 to 13 different embodiments of the arrangement of thermoplates.

The embodiment in FIG. 1 shows the schematic illustration of a plant with a main reactor 1 and a postreactor 2 attached thereto by a flange connection. The main reactor 1 is designed as a tube bundle apparatus through whose catalyst tubes the reaction gas mixture, indicated by arrows, flows from the top downward. The coolant 4 flows through the intermediate space between the catalyst tubes.

The postreactor 2 is designed as an apparatus with thermoplates 5 through which a coolant 4 likewise flows. The intermediate space between the thermoplates 5 is charged in the lower region with a solid-state catalyst. It is evident from the illustration in FIG. 1 that the space between the thermoplates 5 in the upper region of the postreactor 2 is empty. As a result, this part of the postreactor 2 functions as an integrated device 3 for intermediate cooling.

Figure 2:
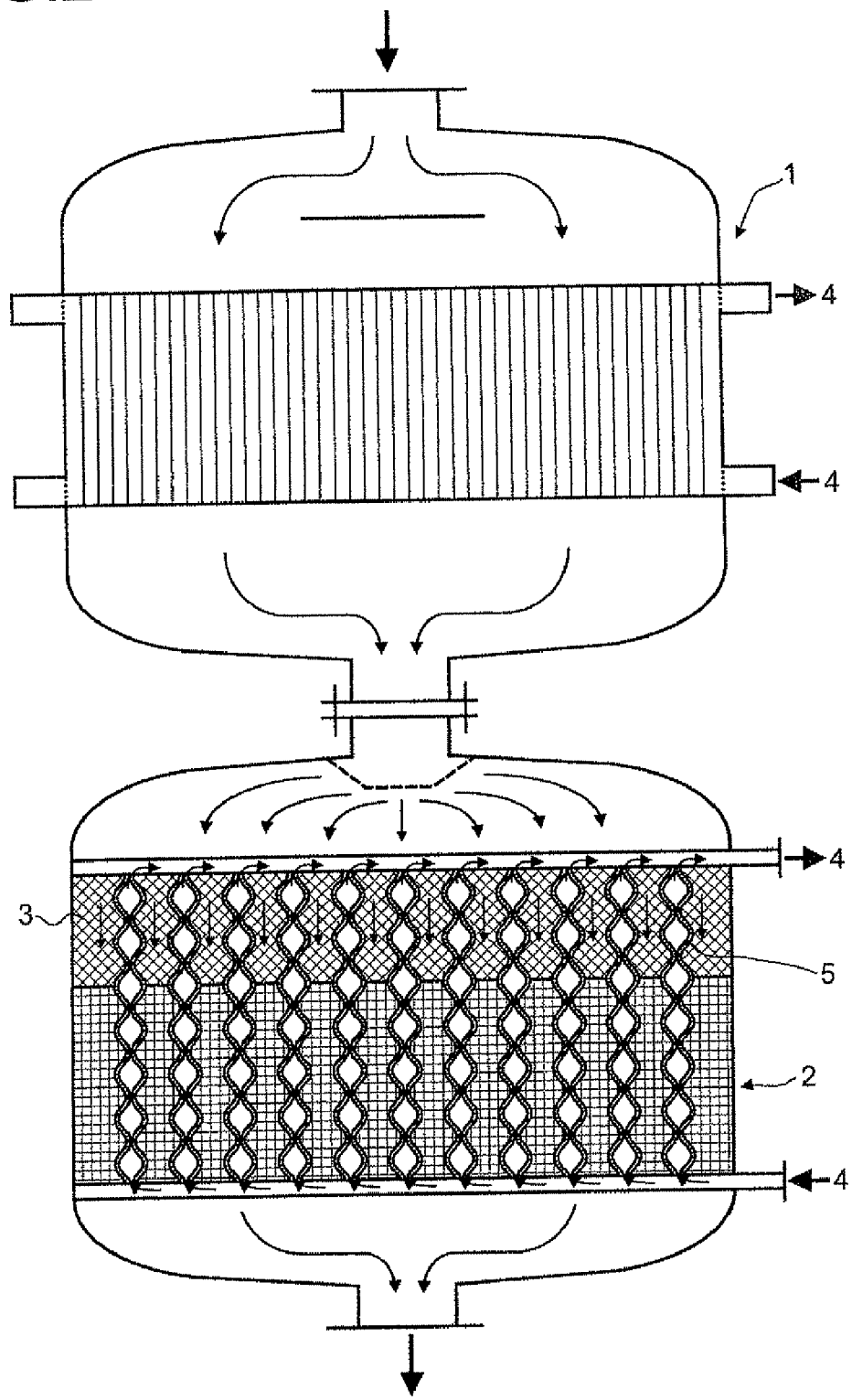

The embodiment in FIG. 2 differs from the embodiment shown in FIG. 1 in that the region which functions as an intermediate cooler 3 in the postreactor 2 is charged with an inert material.

Figure 3:
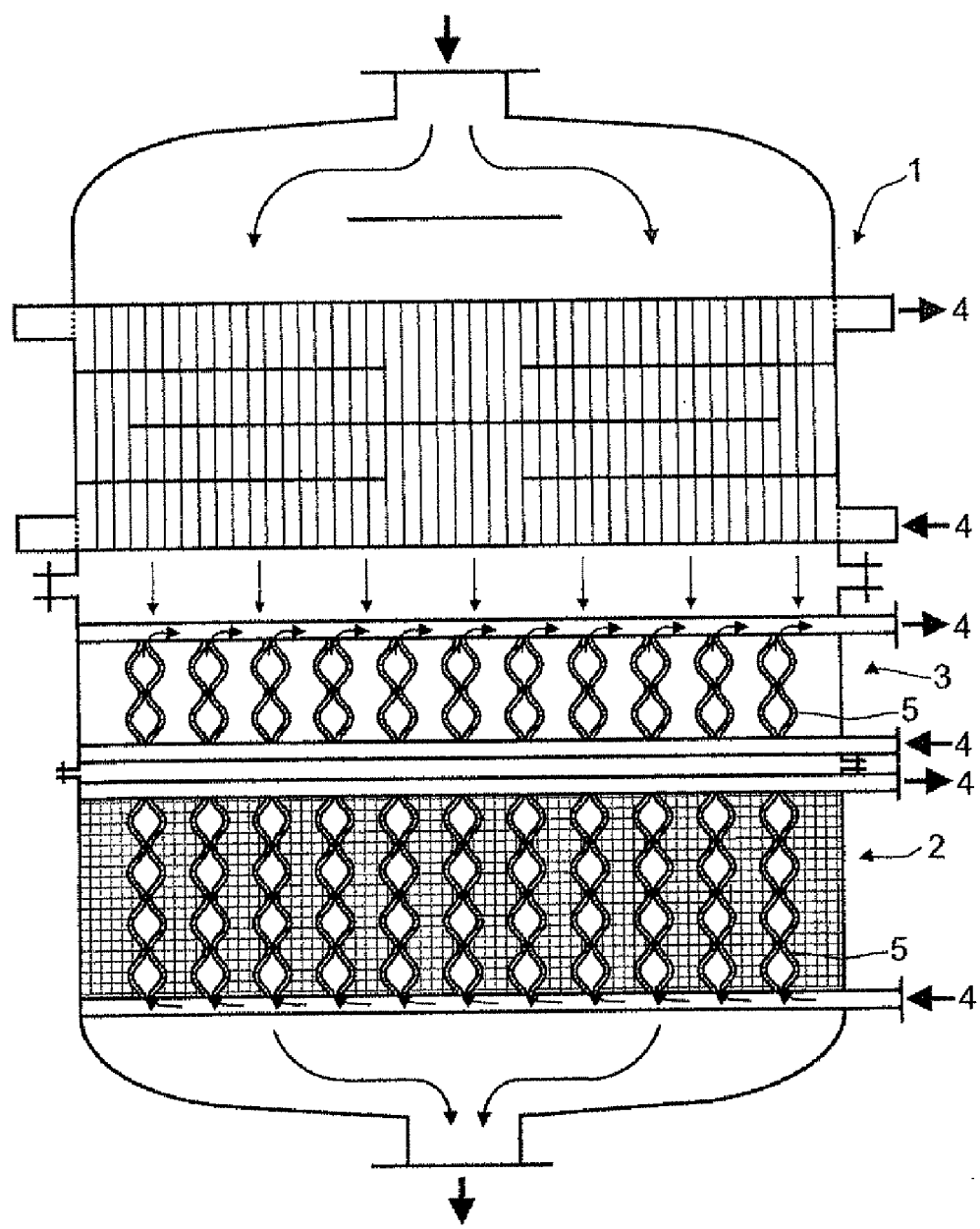

FIG. 3 shows an embodiment with main reactor 1, postreactor 2 and device for intermediate cooling 3 integrated in a single apparatus, the device for intermediate cooling 3 and the postreactor 2 each being equipped with thermoplates 5. Main reactor 1, postreactor 2 and device for intermediate cooling 3 each have separate circuits for the coolant 4. The main reactor 1 is equipped with a bundle of catalyst tubes and also with deflection plates.

Figure 4:
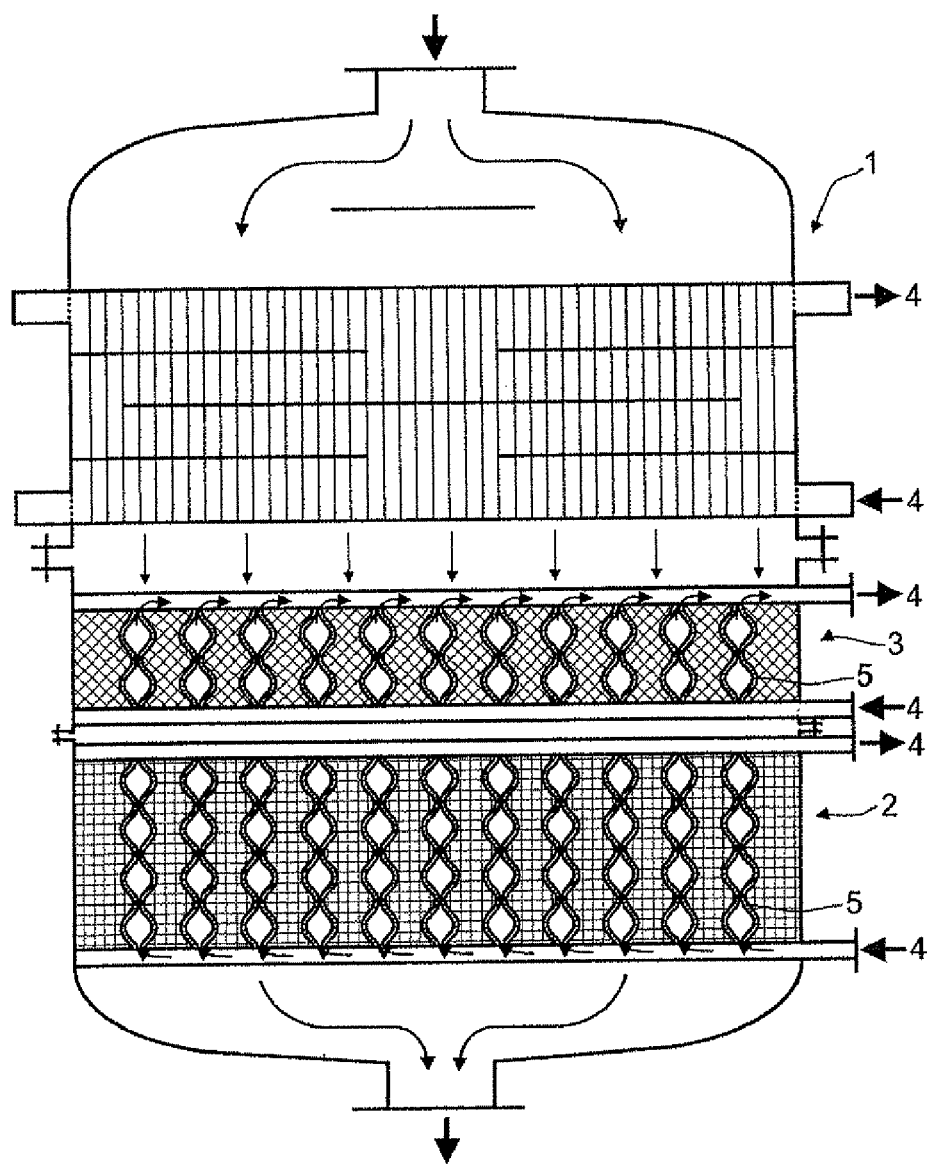

FIG. 4 differs from the embodiment shown in FIG. 3 only in that inert material is installed between the thermoplates 5 in the device for intermediate cooling 3.

Figure 5:
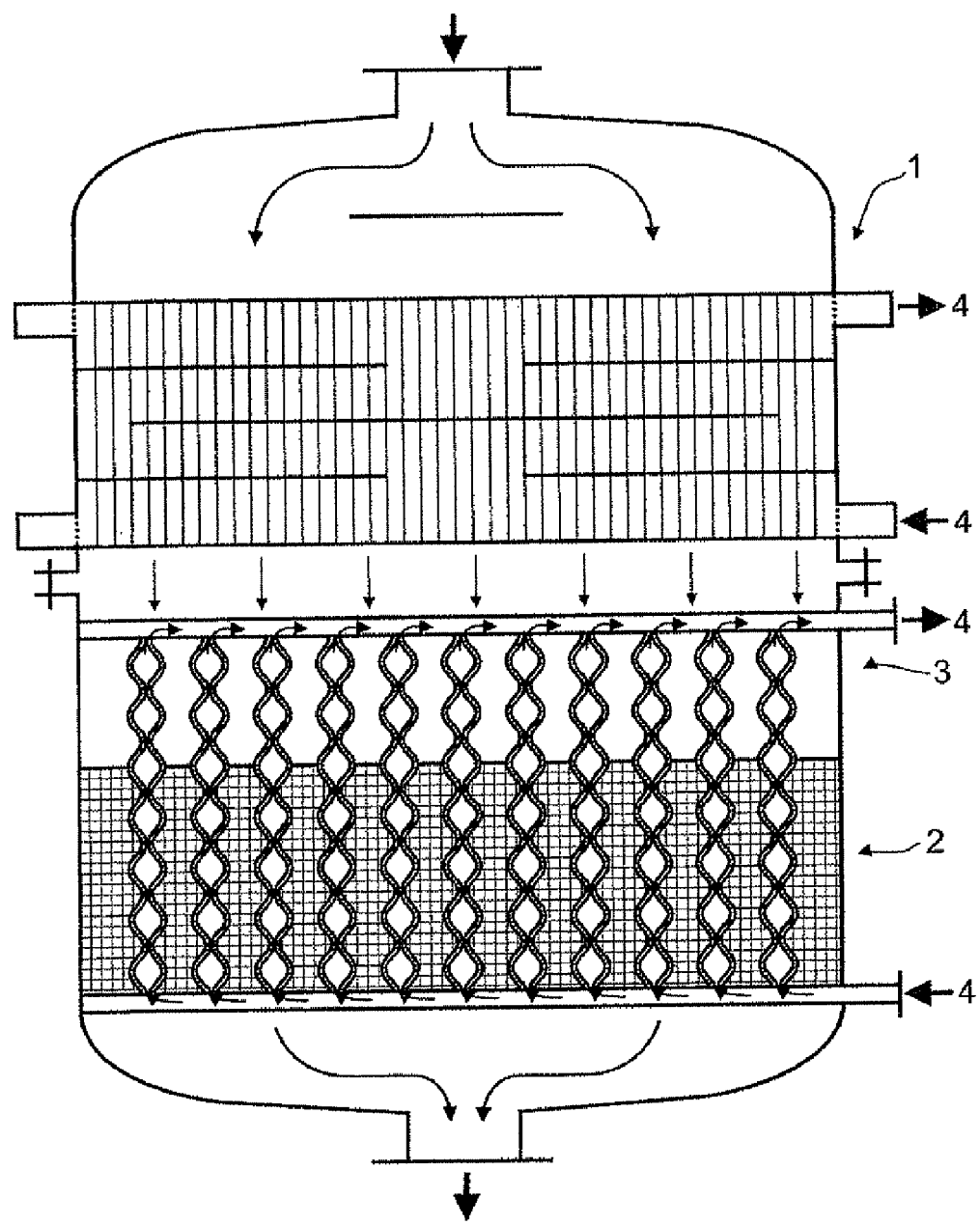

The embodiment in FIG. 5 differs from the embodiment shown in FIG. 3 in that the device for intermediate cooling 3 is integrated into the postreactor 2.

Figure 6:
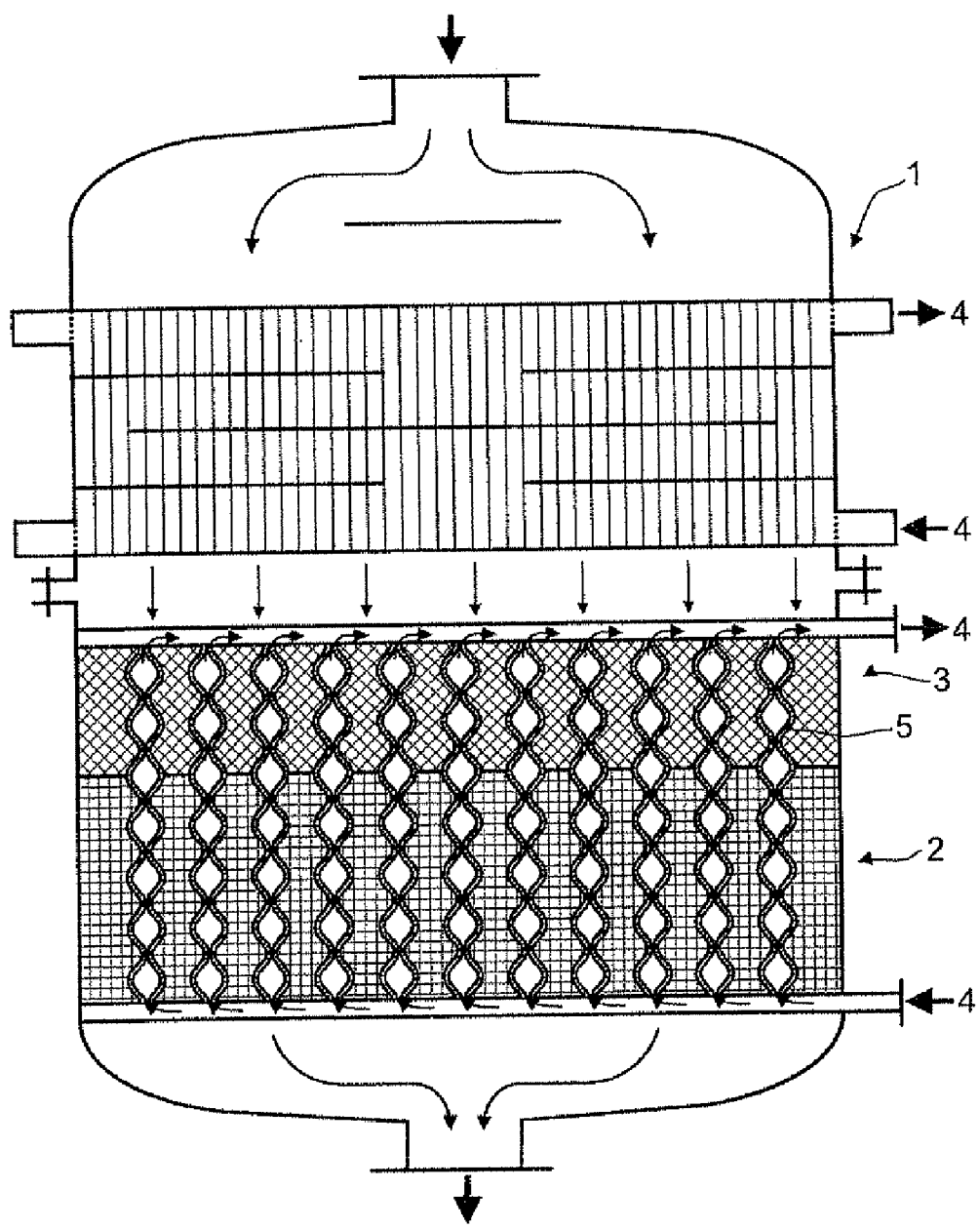

The embodiment shown in FIG. 6 differs from the embodiment in FIG. 5 only in that, in the region which functions as a device for intermediate cooling, an inert material is installed between the thermoplates 5.

Figure 7:
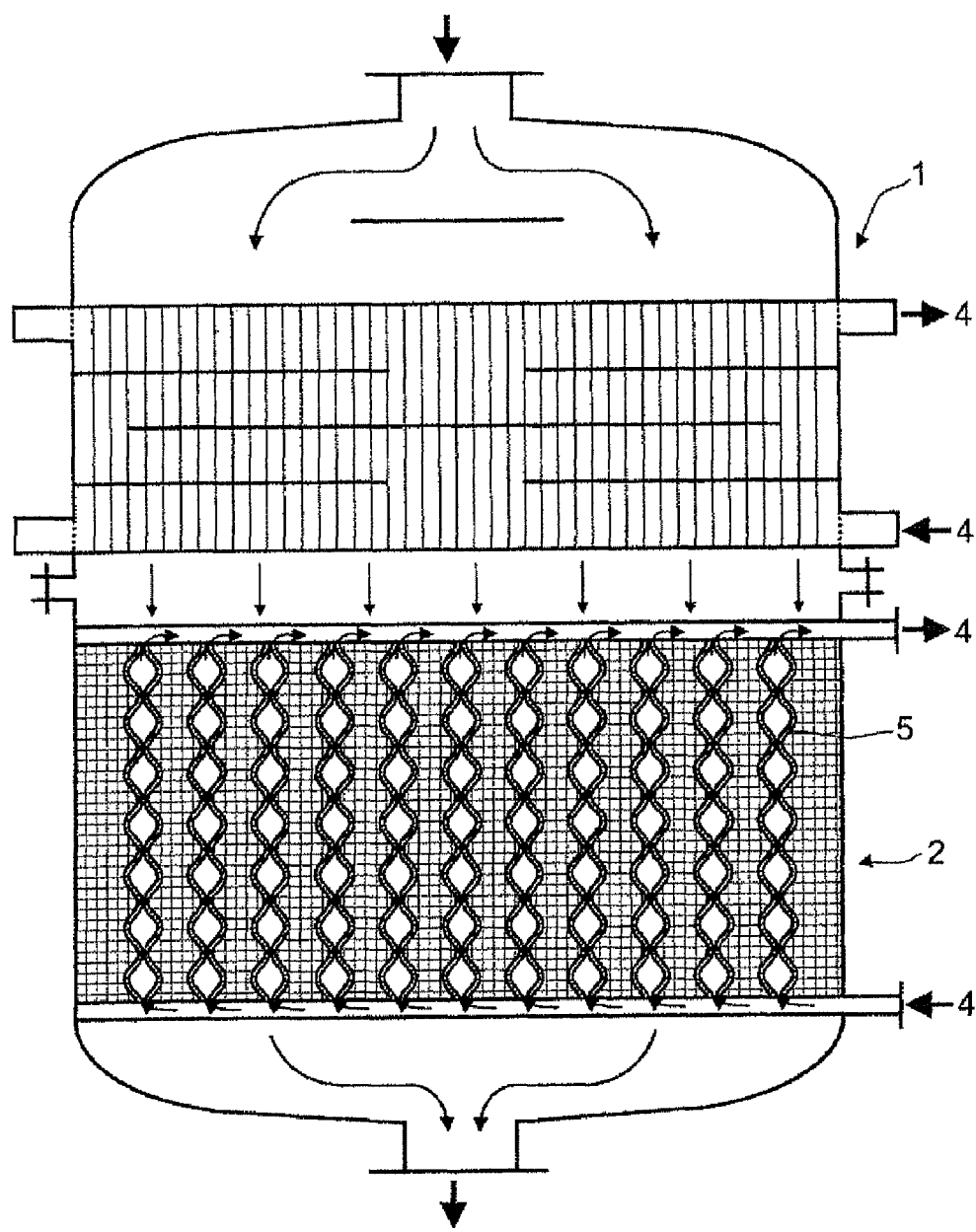

The embodiment in FIG. 7 differs from the embodiment in FIG. 6 in that the postreactor 2, the region between the thermoplates 5, is filled entirely with solid-state catalyst.

Figure 8:
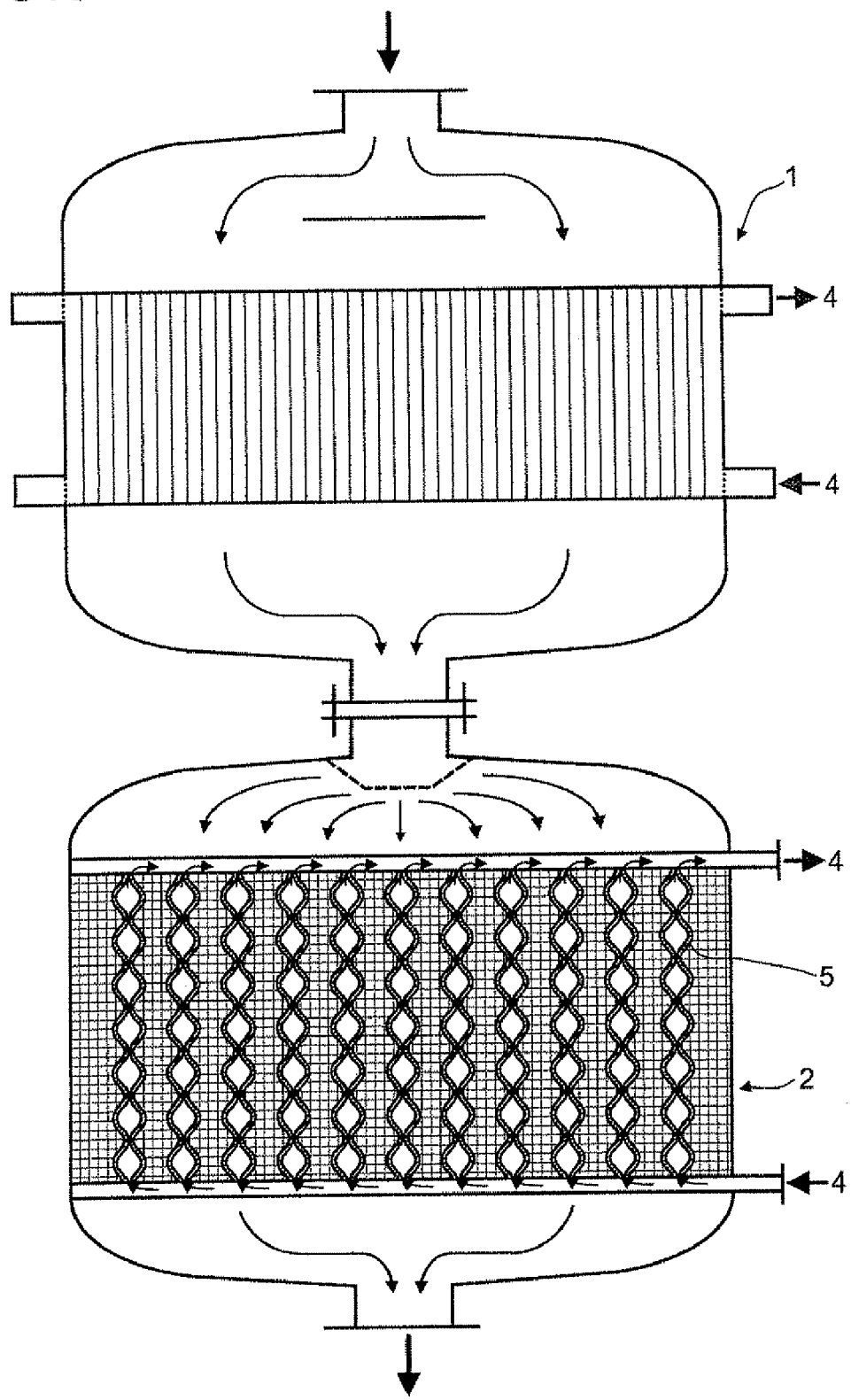

In FIG. 8 too, the region between the thermoplates 5 in the postreactor 2 is filled entirely with a solid catalyst material.

Figure 9A:
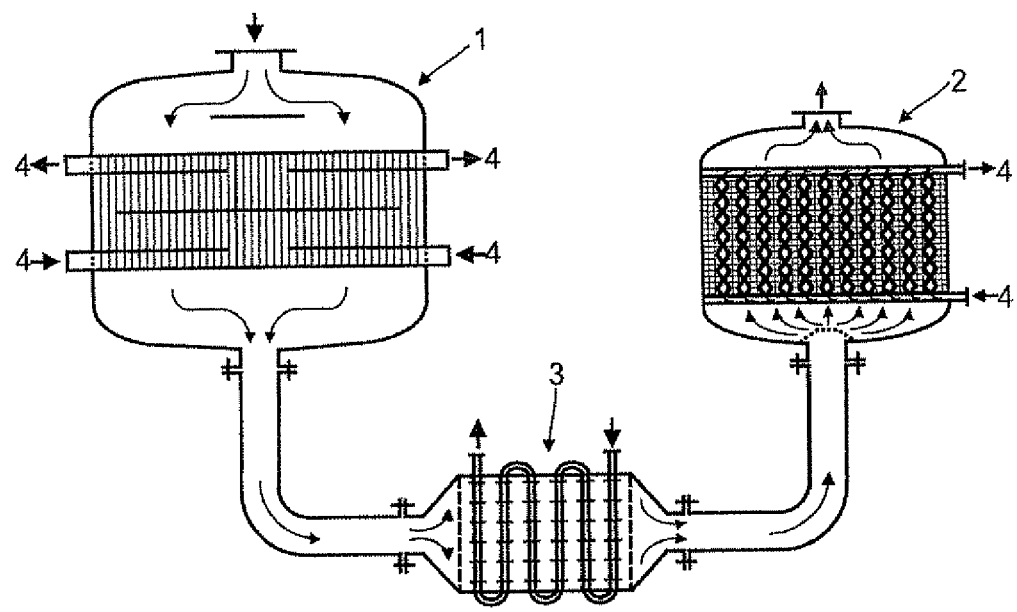
Figure 9B:
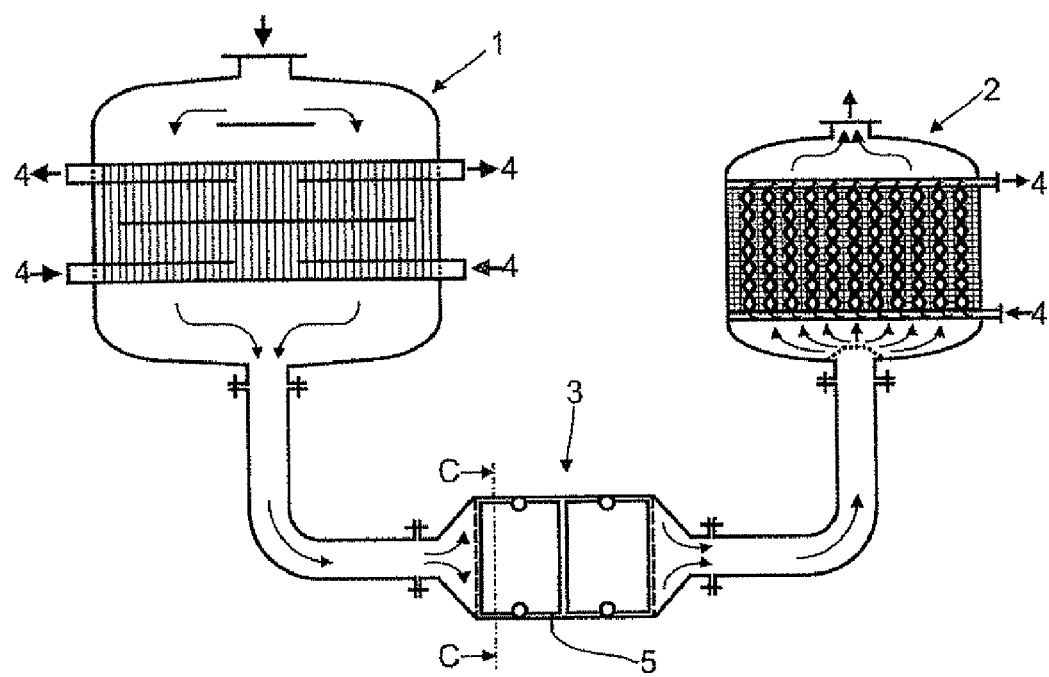
Figure 9C:
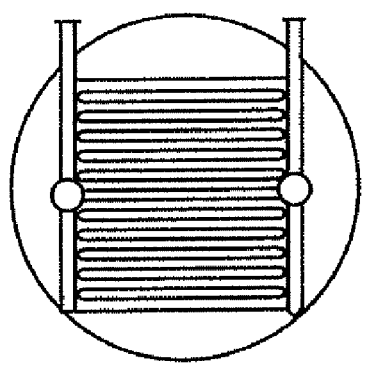
Figure 10:
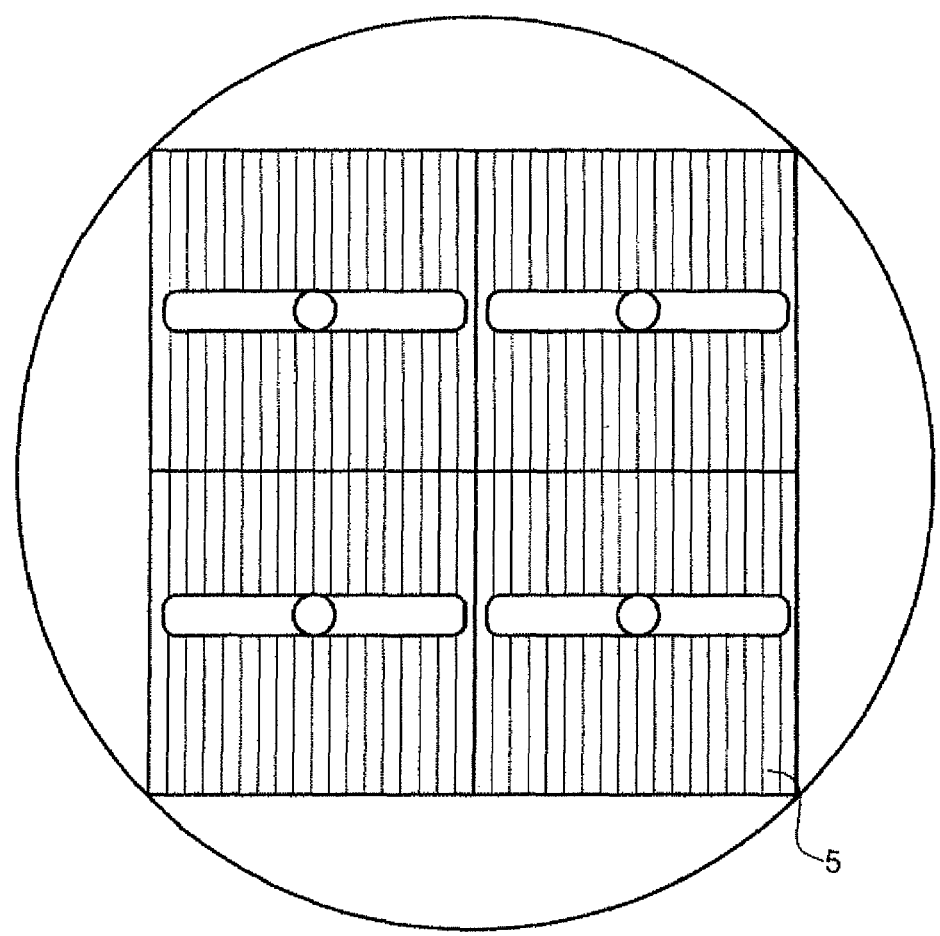
Figure 11:
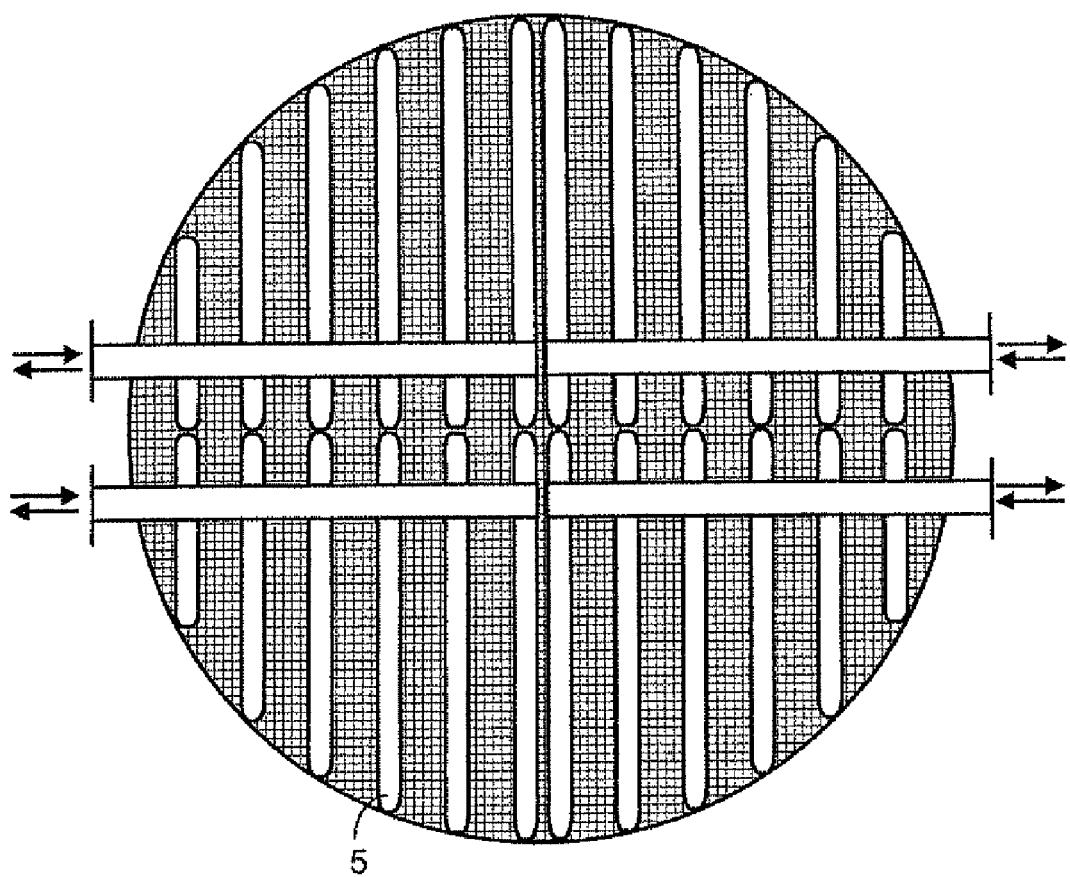
Figure 12:
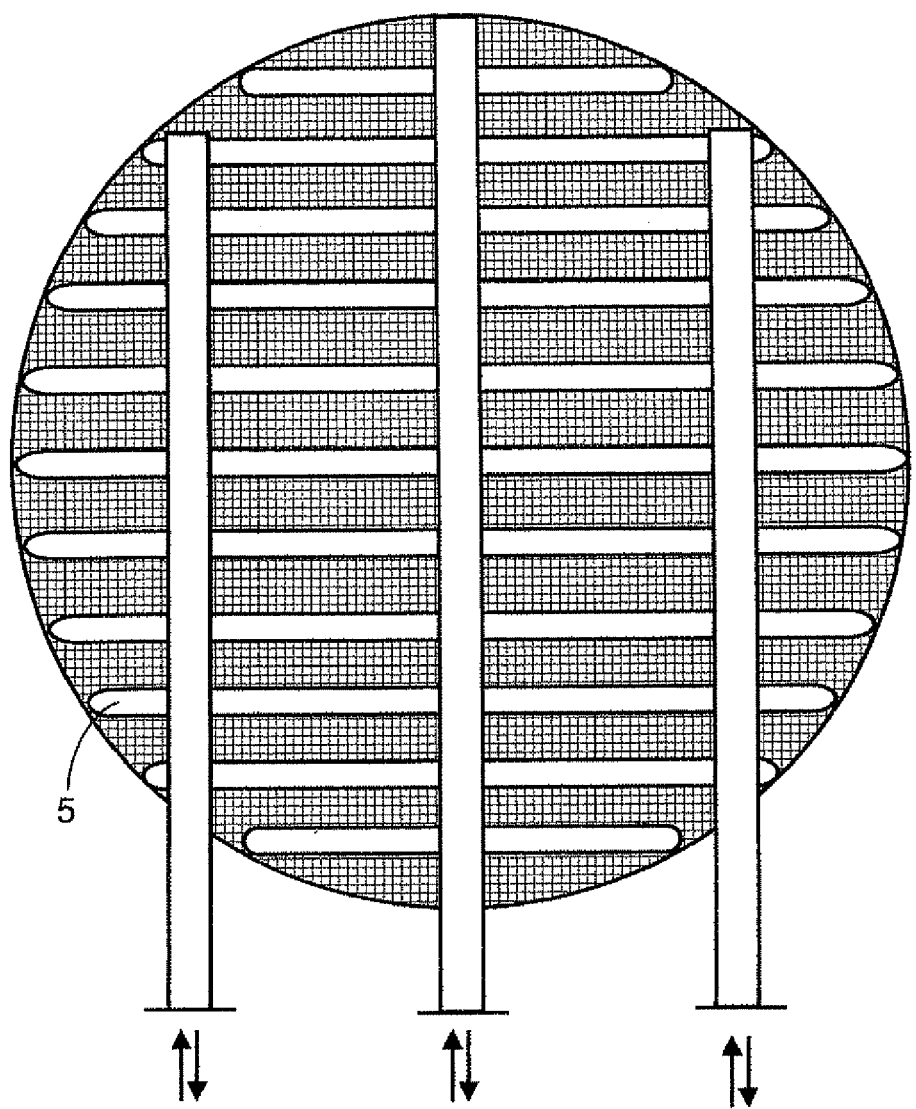
Figure 13:
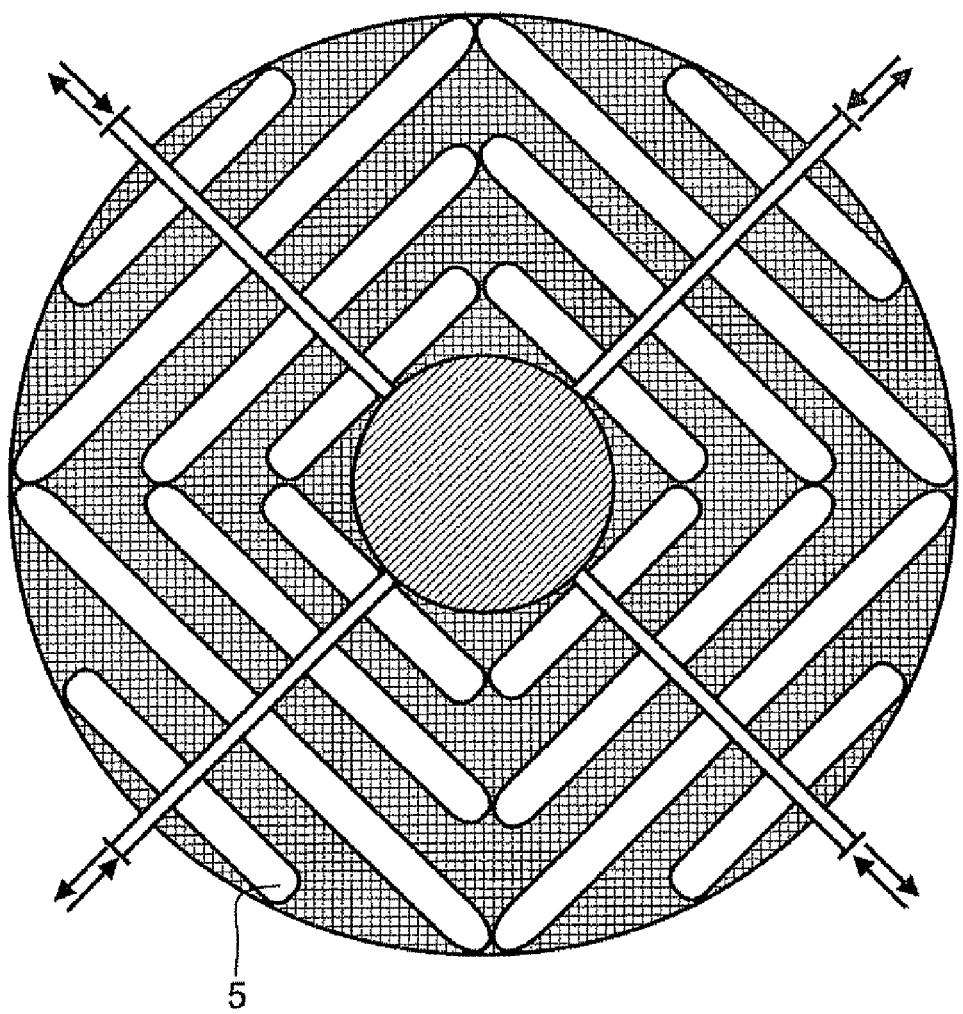

The embodiments in FIGS. 9A and 9B show a plant with main reactor 1 and postreactor 2 arranged alongside one another, with a cooling coil (FIG. 9A) or thermoplates (FIG. 9B) arranged in the intermediate cooler 3. FIG. 9C shows the section C-C through the intermediate cooler 3 from FIG. 9B.

FIGS. 10 to 13 show various arrangements of thermoplates 5 in the plant used to carry out the process according to the invention.

What is claimed is:

1. A process comprising:
   (a) providing a reactant comprising a component selected from the group consisting of o-xylene, naphthalene and mixtures thereof, and a gas comprising oxygen;
   (b) reacting the reactant and the gas in a reaction system, in the presence of a catalyst, to form phthalic anhydride;
   wherein the reaction system comprises: (i) at least two reaction zones, each reaction zone cooled with a coolant; and (ii) an intermediate cooling zone disposed between a first of the at least two reaction zones and a second of the at least two reaction zones; and wherein the coolant entering the first of the at least two reaction zones has a temperature which is more than 20° C. higher than a temperature of the coolant entering the second of the at leas two reaction zones.

2. The process according to claim 1, wherein the reaction system has two cooled reaction zones.

3. The process according to claim 2, wherein the two cooled reaction zones are a cooled main reactor and a cooled postreactor.

4. The process according to claim 3, wherein the coolant entering the main reactor has a temperature of 320 to 380° C., and wherein the coolant entering the postreactor has a temperature of 250 to 320° C.

5. The process according to claim 4, wherein the temperature of the coolant entering the postreactor is 270 to 300° C.

6. The process according to claim 5, wherein the temperature of the coolant entering the postreactor is 280 to 290° C.

7. The process according to claim 3, wherein the postreactor is operated at a residual conversion of from 5 to 10% based on an overall conversion of the reaction system.

8. The process according to claim 3, wherein the postreactor is operated at a residual conversion up to 15% based on an overall conversion of the reaction system.

9. The process according to claim 3, wherein the postreactor is operated at a residual conversion up to 20% based on an overall conversion of the reaction system.

10. The process according to claim 1, wherein heat is removed from the reaction system by evaporative cooling of the coolant.

11. The process according to claim 1, wherein the at least two reaction zones and the intermediate cooling zone are disposed in a single apparatus comprising thermoplates through which coolant flows.

12. The process according to claim 3, further comprising a first cooling circuit and a second cooling circuit, wherein the first cooling circuit feeds coolant to the main reactor, and wherein the second cooling circuit feeds coolant to the intermediate cooling zone and the postreactor.

13. The process according to claim 1, wherein the intermediate cooling zone comprises an inert bed.

14. The process according to claim 1, wherein one or more of the at least two reaction zones comprises a tube bundle apparatus.

15. The process according to claim 1, wherein the first of the at least two reaction zones comprises a tube bundle apparatus, and wherein the second or another of the at least two reaction zones comprises an apparatus having thermoplates.

* * * * *